(12) United States Patent
Fisher et al.

(10) Patent No.: US 6,344,197 B2
(45) Date of Patent: *Feb. 5, 2002

(54) METHODS FOR TREATING SEPSIS

(75) Inventors: Charles Jack Fisher, Carmel; Sau-Chi Betty Yan, Indianapolis, both of IN (US)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/425,181

(22) Filed: Oct. 22, 1999

Related U.S. Application Data

(60) Provisional application No. 60/105,239, filed on Oct. 22, 1998.

(51) Int. Cl.[7] .......................... A61K 38/17; A61K 38/48
(52) U.S. Cl. .......................... 424/94.64; 514/12; 514/21
(58) Field of Search .............................. 514/8, 12, 21; 424/94.64; 435/212, 219; 530/350, 351, 380, 395

(56) References Cited

U.S. PATENT DOCUMENTS

| | | | |
|---|---|---|---|
| 4,775,624 A | 10/1988 | Bang et al. | 435/226 |
| 4,981,952 A | 1/1991 | Yan | 530/384 |
| 4,992,373 A | 2/1991 | Bang et al. | 435/226 |
| 5,009,889 A | * 4/1991 | Taylor, Jr. et al. | 424/94.64 |
| 5,093,117 A | * 3/1992 | Lawrence et al. | 424/85.8 |
| 5,171,739 A | 12/1992 | Scott et al. | 514/12 |
| 5,198,541 A | 3/1993 | Elsbach et al. | 435/69.1 |
| 5,308,834 A | 5/1994 | Scott et al. | 514/12 |
| 5,453,373 A | 9/1995 | Gerlitz et al. | 435/240.2 |
| 5,478,558 A | 12/1995 | Eibl et al. | 424/94.63 |
| 5,516,650 A | 5/1996 | Foster et al. | 435/68.1 |
| 5,550,036 A | 8/1996 | Grinnell | 435/69.1 |
| 5,607,916 A | 3/1997 | Pereira et al. | 514/12 |
| 5,627,262 A | 5/1997 | Pereira | 530/324 |
| 5,733,872 A | 3/1998 | Little | 514/12 |
| 5,753,620 A | 5/1998 | Friedmann et al. | 514/12 |
| 5,756,464 A | 5/1998 | Scannon et al. | 514/12 |
| 6,008,199 A | 12/1999 | Grinnell et al. | 514/21 |

FOREIGN PATENT DOCUMENTS

| | | |
|---|---|---|
| EP | 0 445 939 | 9/1991 |
| WO | WO 97/20043 | 6/1997 |
| WO | WO 99/20293 | 4/1999 |

OTHER PUBLICATIONS

Elsbach, "Separation and Purification of a Potent Bactericidal/Permeability–increasing Protein and a Closely Associated Phospholiapase $A_2$ form Rabbit Polymorphonuclear Leukocytes", *J. Biol. Chem.* 254:11000, 1979.

Weiss et al., "Cellular and Subcellular Localization of the Bactericidal/Permeability–Increasing Protein of Neutrophils", *Blood* 69:652, 1987.

Mesters, et al., "Factor VIIa and Antithrombin III Activity During Severe Sepsis and Septic Shock in Neutropenic Patients", *Blood* 88:881–886, 1996.

Fourrier, et al., "Septic Shock, Multiple Organ Failure, and Disseminated Intravascular Coagulation", *Chest* 101:816–823, 1992.

Natanson, et al., "Selected Treatment Strategies for Septic Shock Based on Proposed Mechanisms of Pathogenesis", *Ann. Intern. Med* 120:771–783, 1994.

Gibaldi, "Anatomy of an Antibody,and Related Misadventures in Developing an Effective Treatment for Septic Shock", *Pharmacotherapy* 13(4) :302–308, 1993.

Parrillo, "Pathogenetic Mechanisms of Septic Shock", *N. Engl. J. Med.* 328(20) :1471–1477, 1993.

Taylor, et al., "Protein C Prevents the Coagulopathic and Lethal Effects of *Escherichia coli* Infusion in the Baboon", *J. Clin. Invest.* 79:918–25, 1987.

Gerson, et al., "Severe Acquired Protein C Deficiency in Purpura Fulminans Associated with Disseminated Intravascular Coagulation: Treatment with Protein C Concentrate", *Pediatrics* 91(2) :418–422, 1993.

Smith, et al., "Successful Treatment of Meningoccai Induced Protein C Deficiency/Purpura Fulminans in Children with Protein C Concentrate and Heparin", *Thromb. Haemost,* PS1709, p419, 1997.

Rintala, et al., "Protein C in the Treatment of Coagulopathy in Meningococcal Disease", *Lancet* 347:1767, 1996.

Rivard, et al., "Treatment of Purpura Fulminans in Meningococcemia with Protein C Concentrate", *J.Pediatr.* 126:646–652, 1995.

Fisher, et al., "Human neutrophil bactericidal/permeability–increasing protein reduces mortality rate from endotoxin challenge: A placebo–controlled study", *Crit. Care Med.,* 22(4) : 553–558, 1994.

Gray et al., "Cloning of the CDNA of a Human Neutrophil Bactericidal Protein", *J. Biol. Chem* 264(16) :9505, 1989.

(List continued on next page.)

Primary Examiner—Jeffrey E. Russel
(74) *Attorney, Agent, or Firm*—Brian P. Barrett

(57) ABSTRACT

The present invention provides a method of treatment for patients with sepsis. The claimed treatment is a combination therapy with protein C and BPI protein. Combining protein C, with its anti-coagulant/anti-inflammatory properties, and BPI, with its bactericidal and endotoxin neutralizing activities, provides an effective, synergistic therapy for sepsis that will reduce or ameliorate the adverse events and improve the clinical outcome of septic patients.

20 Claims, No Drawings

OTHER PUBLICATIONS

Ooi et al., "Endotoxin–neutralizing Properties of the 25 kD N–Terminal Fragment and a Newly Isolated 30kD C–Terminal Fragment of the 55–60 kD Bactericidal/Permeability–increasing Protein of Human Neutrophils", *J. Exp. Med, 174*:649, 1991.

Gazzano–Santoro et al., "High–Affinity Binding of a Bactericidal/Permeability–Increasing Protein and a Recombinant Amino–Terminal Fragment to the Lipid A Region of Lipopolysaccharide", *Infect. Immun. 60(11)* :4754–4761, 1992.

Grinnell, et al., "Trans–Activated Expression of Fully Gamma–Carboxylated Recombinant Human Protein C, An Antithrombotic Factor", *Bio/Technology 5*:1189–1192, 1987.

McGrogan, et al, "Molecular Cloning and Expression of Two Forms of Human Protease Nexin I". *Biotechnology, 6*: 172–177 (Feb. –1988).

* cited by examiner

METHODS FOR TREATING SEPSIS

This application claims priority of Provisional Application Ser. No. 60/105,239 filed Oct. 22, 1998.

FIELD OF THE INVENTION

This invention relates to medical science particularly the treatment of sepsis with protein C in combination with Bactericidal Permeability Increasing (BPI) Protein.

BACKGROUND OF THE INVENTION

Protein C is a serine protease and naturally occurring anticoagulant that plays a role in the regulation of hemostasis by inactivating Factors Va and VIIIa in the coagulation cascade. Human protein C circulates as a 2-chain zymogen, but functions at the endothelial and platelet surface following conversion to activated protein C (aPC) by limited proteolysis with thrombin in complex with the cell surface membrane protein, thrombomodulin.

In conjunction with other proteins, aPC functions as perhaps the most important down-regulator of blood coagulation resulting in protection against thrombosis. In addition to its anti-coagulation functions, aPC has anti-inflammatory effects through its inhibition of cytokine generation (e.g. TNF and IL-1) and also exerts profibrinolytic properties that facilitate clot lysis. Thus, the protein C enzyme system represents a major physiological mechanism of anti-coagulation, anti-inflammation, and fibrinolysis.

Bactericidal permeability-increasing protein (BPI), is a protein isolated from the granules of mammalian polymorphonuclear neutrophils (PMNs). Human BPI has been isolated from PMNs by acid extraction combined with chromatography (Elsbach, 1979, *J. Biol. Chem.* 254:11000; Weiss et al. 1987, *Blood* 69:652), and has been shown to have potent bactericidal activity against a broad spectrum of Gram-negative bacteria. In addition to its bactericidal effect on Gram negative bacteria, BPI is also capable of binding to and neutralizing lipopolysaccharide (LPS) which is also known as endotoxin because of the inflammatory response that it stimulates.

Sepsis, which includes severe sepsis and septic shock, is a systemic inflammatory response to infection or trauma, associated with and mediated by the activation of a number of host defense mechanisms including the cytokine network, leukocytes, and the complement and coagulation/fibrinolysis systems. [Mesters, et al., *Blood* 88:881–886, 1996]. Disseminated intravascular coagulation [DIC], with widespread deposition of fibrin in the microvasculature of various organs, is an early manifestation of sepsis/septic shock. DIC is an important mediator in the development of the multiple organ failure syndrome and contributes to the poor prognosis of patients with septic shock. [Fourrier, et al., *Chest* 101:816–823, 1992].

Sepsis may be caused by bacterial (either Gram negative or Gram positive), fungal, viral and other infections as well as by non-infective stimuli such as multiple trauma, severe burns, and organ transplantation.

Although sepsis can follow any bacterial infection, it is often associated with a gram negative infection. Sepsis usually begins with tremor, fever, falling blood pressure, rapid breathing and heart beat, and skin lesions. Within hours or days it can progress to spontaneous clotting in the blood vessels, severe hypotension, multiple organ failure, and death.

Most of-the damage comes not from the invading bacteria but from enotoxin. This effect by endotoxin is manifested by its binding to cells such as monocytes/macrophages or endothelial cells, and triggering them to produce various mediators such as tumor necrosis factor-alpha (TNF-$\alpha$), and various interleukins (IL-1, IL-6, and IL-8). Production of excessive TNF-$\alpha$) IL-1, IL-6, and IL-8 can elicit septic shock.

There have been numerous recent attempts to treat sepsis in humans, for the most part using agents that block inflammatory mediators associated with the pathophysiology of this disease. However, clinical studies with a variety of agents that block inflammatory mediators have been unsuccessful [reviewed in Natanson, et al., *Ann. Intern. Med* 120:771–783, 1994; Gibaldi, *Pharmacotherapy* 13:302–308, 1993]. Since many of the mediators involved in inflammation are compensatory responses, and therefore have salutary effects, some investigators have suggested that blocking their action may not be appropriate [e.g., Parrillo, *N. Engl. J. Med.* 328:1471–1477, 1993].

Several encouraging studies using protein C in various animal models of sepsis have been reported. A study in a baboon sepsis model by Taylor, et al., [*J. Clin. Invest.* 79:918–25, 1987], used plasma-derived human activated protein C. The animals were treated prophylactically (i.e., the aPC was given at the start of the two hour infusion of the $LD_{100}$ *E. coli*). Five out of five animals survived 7 days and were considered permanent survivors to the experimental protocol. In control animals receiving an identical infusion of *E. coli*, five out of five animals died in 24 to 32 hours. In addition, plasma-derived human protein C zymogen has been used as a successful adjunct to aggressive conventional therapy in the management of human patients with purpura fulminans in bacterial sepsis (Gerson, et al., *Pediatrics* 91:418–422, 1993; Smith, et al., *Thromb. Haemost*, PS1709, p419, 1997; Rintala, et al., *Lancet* 347:1767, 1996; Rivard, et al., *J. Pediatr.* 126:646–652, 1995).

Recombinant BPI protein has been shown to neutralize lethal and sublethal effects of endotoxin administered to mice, rats, and rabbits (Fisher, et al., Crit. Care Med., 22(4): 553–558, 1994). Because of this ability to neutralize endotoxin and its Gram-negative bactericidal activity, BPI can be utilized for the treatment of human patients suffering from diseases caused by gram-negative bacteria, including bacteremia, endotoxemia, and sepsis.

The present invention is the first to describe the combination of aPC with BPI in the treatment of sepsis. The combination of aPC and BPI results in a synergy that allows the reduction of the dosages of both aPC and BPI and an improvement of clinical outcome of the patient being treated. The reduction of the dosages of the agents in combination therapy in turn results in reduced side effects that may occur with either agent. Therefore, combining aPC, with its anti-coagulant/anti-inflammatory properties, and BPI, with its bactericidal and endotoxin neutralizing activities will provide an effective synergistic therapy for sepsis that will reduce or ameliorate the adverse events and improve the clinical outcome of septic patients.

SUMMARY OF THE INVENTION

The present invention provides a method of treating a patient suffering from sepsis which comprises administering to said patient a pharmaceutically effective amount of protein C in combination with bactericidal permeability-increasing (BPI) protein.

The present invention further provides a method of treating sepsis in a patient in need thereof, which comprises administering to said patient a pharmaceutically effective amount of BPI protein and activated protein C such that an activated protein C plasma level of about 2 ng/ml to about 300 ng/ml is achieved.

DETAILED DESCRIPTION OF THE INVENTION

For purposes of the present invention, as disclosed and claimed herein, the following terms are as defined below.

Protein C refers to a vitamin K dependent serine protease with anticoagulant, anti-inflammatory, and profibrinolytic properties which includes, but is not limited to, plasma derived and recombinant produced protein C. Protein C includes and is preferably human protein C although protein C may also include other species or derivatives having protein C proteolytic, amidolytic, esterolytic, and biological (anticoagulant, pro-fibrinolytic, and anti-inflammatory) activities. Examples of protein C derivatives are described by Gerlitz, et al., U.S. Pat. No. 5,453,373, and Foster, et al., U.S. Pat. No. 5,516,650, the entire teachings of which are hereby included by reference.

Zymogen—an enzymatically inactive precursor of a proteolytic enzyme. Protein C zymogen, as used herein, refers to secreted, inactive forms, whether one chain or two chains, of protein C.

Activated protein C or aPC refers to protein C zymogen which has been converted by limited proteolysis to its activated form. aPC includes and is preferably human protein C although aPC may also include other species or derivatives having protein C proteolytic, amidolytic, esterolytic, and biological (anticoagulant or pro-fibrinolytic) activities. Examples of protein C derivatives are noted above in the description of protein C.

r-hPC—recombinant human protein C zymogen.

r-aPC—recombinant activated protein C, preferably produced by activating r-hPC in vitro or by direct secretion of the activated form of protein C from procaryotic cells, eukaryotic cells, and transgenic animals or plants, including, for example, secretion from human kidney 293 cells as a zymogen then purified and activated by techniques well known to the skilled artisan and demonstrated in Yan, U.S. Pat. No. 4,981,952, and Cottingham, WO97/20043, the entire teachings of which are herein incorporated by reference.

Plasma derived activated protein C—activated protein C produced by activating plasma protein C as described in Eibl, U.S. Pat. No. 5,478,558, the entire teaching of which is herein incorporated by reference.

Continuous infusion—continuing substantially uninterrupted the introduction of a solution into a vein for a specified period of time.

Bolus injection—the injection of a drug in a defined quantity (called a bolus) over a period of time up to about 120 minutes.

Suitable for administration—a lyophilized formulation or solution that is appropriate to be given as a therapeutic agent.

Unit dosage form—refers to physically discrete units suitable as unitary dosages for human subjects, each unit containing a predetermined quantity of active material calculated to produce the desired therapeutic effect, in association with a suitable pharmaceutical excipient.

Pharmaceutically effective amount—represents an amount of protein C of the present invention that is capable of treating sepsis in humans. The particular dose of protein C administered according to this invention will, of course, be determined by the attending physician evaluating the particular circumstances surrounding the case.

BPI protein—includes naturally and recombinantly produced bactericidal permeability increasing (BPI) protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The complete amino acid sequence of human BPI, as well as the nucleotide sequence of DNA encoding BPI have been elucidated by Gray et al., 1989, *J. Biol. Chem* 264:9505. Recombinant genes encoding and methods for expression of BPI proteins, including BPI holoprotein and fragments of BPI are disclosed in U.S. Pat. No. 5,198,541, herein incorporated by reference.

The present invention relates to the treatment of sepsis with protein C in combination with BPI protein. The combination of protein C and BPI results in a synergy that allows the reduction of the dosages of both protein C and BPI and an improvement of clinical outcome of the patient being treated. The reduction of the dosages of the agents in combination therapy in turn results in reduced side effects that may occur with either agent. Therefore, combining protein C, with its anti-coagulant/anti-inflammatory properties, and BPI, with its bactericidal and endotoxin neutralizing activities will provide an effective synergistic therapy for sepsis that will reduce or ameliorate the adverse events and improve the clinical outcome of septic patients.

The protein C administered according to this invention may be generated and/or isolated by any means known in the art or as described in U.S. Pat. No. 4,981,952, and U.S. Pat. No. 5,550,036, herein incorporated by reference. For example, the invention provides a method for producing and secreting full-length, soluble protein C, or biologically active polypeptide variants of protein C from a cell which comprises (a) constructing a vector comprising DNA encoding protein C; (b) transfecting the cell with the vector; and (c) culturing the cell so transfected in culture medium under conditions such that full length soluble protein C or biologically active polypeptide variants of protein C, is secreted. Further, the cell is a eukaryotic cell, e.g. mammalian cell such as Syrian hamster AV12 cell, human embryonic 293 cell, or Baby Hamster Kidney cell.

The protein C used in such combination can be formulated according to known methods to prepare pharmaceutically useful compositions. For example, a desired formulation would be one that is a stable lyophilized product of high purity comprising a bulking agent such as sucrose, a salt such as sodium chloride, a buffer such as sodium citrate and protein C or aPC.

The protein C will be administered parenterally to ensure its delivery into the bloodstream in an effective form by injecting the appropriate dose as continuous infusion for about 1 hour to about 240 hours.

In conjunction with treatment with BPI protein, the amount of protein C administered will be from about 5.0 µg/kg/hr to about 250 µg/kg/hr. Preferably, the protein C administered in combination with BPI protein will be activated protein C. The aPC administered will be from about 1.0 µg/kg/hr to about 50 µg/kg/hr. More preferably the amount of aPC administered will be about 1.0 µg/kg/hr to about 40 µg/kg/hr. While more preferably the amount of aPC administered will be about 1.0 µg/kg/hr to 35 µg/kg/hr. Even more preferably the amount of aPC administered will be about 5.0 µg/kg/hr to 30 µg/kg/hr. Yet even more preferably the amount of aPC administered will be about 15 µg/kg/hr to 30 µg/kg/hr. Still even more preferably the amount of aPC administered will be about 20 µg/kg/hr to 30 µg/kg/hr. The most preferable amount of aPC administered will be about 24 µg/kg/hr. The appropriate dose of aPC administered with BPI protein results in either an improved efficacy or reduction in dose of either agent or both.

The plasma ranges obtained from the amount of aPC administered will be about 2 ng/ml to about 300 ng/ml. The preferred plasma ranges are from about 2 ng/ml to 200 ng/ml. Most preferably, plasma ranges are from about 30 ng/ml to about 150 ng/ml and still more preferably about 100 ng/ml.

Alternatively, the aPC will be administered by injecting one third of the appropriate dose per hour as a bolus injection followed by the remaining two thirds of the hourly dose as continuous infusion for one hour followed by continuous infusion of the appropriate dose for twenty-three hours which results in the appropriate dose administered over 24 hours. In addition, the bolus injection will be administered via an intravenous bag drip pump or syringe pump at about 2 times the normal rate for about 10 to 20 minutes followed by about 1.5 times the normal rate for about 40 to 50 minutes. The normal rate i.e. that rate which has been determined to administer the appropriate dose level of the therapeutic agent per time period, is then continued for up to 240 hours over 24 hours.

BPI protein suitable for use under the present invention includes, but is not limited to, naturally and recombinantly produced BPI protein, for example, a recombinant BPI holoprotein as described in Gray et al. (1989) and U.S. Pat. No. 5,733,872, herein incorporated by reference; natural, synthetic, and recombinant biologically active polypeptide fragments of BPI protein, for example, as described in Ooi et al., J. Exp. Med, 174:649 (1991) and Gazzano-Santoro et al., Infect. Immun. 60:4754–4761 (1992); biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides, examples of which are described in U.S. Pat. Nos. 5,733,872, 5,627,262, 5,753,620, 5,607,916 and 5,756,464, herein incorporated by reference.

Preferably, the BPI protein of the present invention includes biologically active molecules that have the same or similar amino acid sequence as a natural human BPI holoprotein. Nonlimiting examples of such BPI proteins are the 25 Kd N-terminal fragment of natural human BPI protein, described in Ooi et al., (1991), and the recombinant expression product of DNA encoding N-terminal amino acids from 1 to about 193 or 199 of natural human BPI, described in Gazzano-Santoro et al., (1992).

The BPI protein administered according to this invention may be generated and/or isolated by any means known in the art or as described in U.S. Pat. No. 5,308,834, herein incorporated by reference. For example, the invention provides a method for producing and secreting full-length, soluble BPI holoprotein, biologically active polypeptide fragments, or biologically active polypeptide variants of BPI protein or fragments thereof from a cell which comprises (a) constructing a vector comprising DNA encoding BPI; (b) transfecting the cell with the vector; and (c) culturing the cell so transfected in culture medium under conditions such that full length soluble BPI protein, biologically active polypeptide fragments, or biologically active polypeptide variants of BPI protein or fragments thereof, is secreted. Further, the cell is a eukaryotic cell, e.g. mammalian cell such as Syrian hamster AV12 cell, human embryonic 293 cell, or Baby Hamster Kidney cell. Alternatively, the cell is a prokayotic cell, e.g. a yeast cell or a bacterial cell.

The phrase "in combination with" refers to the administration of BPI protein with protein C either simultaneously, sequentially or a combination thereof. The BPI protein utilized and the appropriate dose level is known in the art and described in U.S. Pat. No. 5,756,464, herein incorporated by reference. A skilled artisan recognizes the appropriate dose level to use to achieve a pharmaceutically effective amount for treating sepsis. Pharmaceutically effective compositions comprising BPI protein may be administered systemically or topically. Systemic routes of administration include, intravenous, intramuscular or subcutaneous injection (including into a depot for long-term release), intraocular and retrobulbar, intrathecal, intraperitoneal (e.g. by intraperitoneal lavage), intrapulmonary using aerosalised-or nebulized drug, or transdermal. The preferred route is intravenous administration. When given parenterally, BPI protein compositions are generally injected in doses ranging from about 0.04 ug/kg/hr to about 4 mg/kg/hr. Preferably, the BPI protein is administered at about 4 ug/kg/hr to about 420 ug/kg/hr. More preferably the BPI protein is administered at about 50 ug/kg/hr to about 300 ug/kg/hr. Even more preferably the BPI protein is administered at about 100 ug/kg/hr to about 200 ug/kg/hr. The treatment may continue by continuous infusion or intermittent injection or infusion, at the same, reduced or increased dose per day for, e.g. 24 hours to 240 hours, and additionally as determined by the treating physician. BPI protein is preferably administered intravenously by an initial bolus injection followed by a continuous infusion. A preferred dosing regimen is about 0.1 mg/kg to about 10 mg/kg intravenous bolus of BPI protein followed by intravenous infusion at about 4 ug/kg/hr to about 420 ug/kg/hr, continuing for up to 10 days. Those skilled in the art can readily optimize pharmaceutically effective dosages and administration regimens for therapeutic compositions comprising BPI protein, as determined by good medical practice and the clinical condition of the individual patient.

The combination of the endotoxin neutralization and the Gram-negative bactericidal activity of BPI protein with the anti-coagulation and anti-inflammation activities of aPC results in enhanced efficacy in treating sepsis. The synergy results in the ability to reduce the dosages of the agents in combination therapy.

The following examples are provided merely to further illustrate the present invention. The scope of the invention shall not be construed as merely consisting of the following examples.

PREPARATION 1

Preparation of Human Protein C

Recombinant human protein C (r-hPC) was produced in Human Kidney 293 cells by techniques well known to the skilled artisan such as those set forth in Yan, U.S. Pat. No. 4,981,952, the entire teaching of which is herein incorporated by reference. The gene encoding human protein C is disclosed and claimed in Bang, et al., U.S. Pat. No. 4,775,624, the entire teaching of which is incorporated herein by reference. The plasmid used to express human protein C in 293 cells was plasmid pLPC which is disclosed in Bang, et al., U.S. Pat. No. 4,992,373, the entire teaching of which is incorporated herein by reference. The construction of plasmid pLPC is also described in European Patent Publication No. 0 445 939, and in Grinnell, et al., 1987, *Bio/Technology* 5:1189–1192, the teachings of which are also incorporated herein by reference. Briefly, the plasmid was transfected into 293 cells, then stable transformants were identified, subcultured and grown in serum-free media. After fermentation, cell-free medium was obtained by microfiltration.

The human protein C was separated from the culture fluid by an adaptation of the techniques of Yan, U.S. Pat. No. 4,981,952. The clarified medium was made 4 mM in EDTA before it was absorbed to an anion exchange resin (Fast-Flow Q, Pharmacia). After washing with 4 column volumes of 20 mM Tris, 200 mM NaCl, pH 7.4 and 2 column volumes of 20 mM Tris, 150 mM NaCl, pH 7.4, the bound recombinant human protein C zymogen was eluted with 20 mM Tris, 150 mM NaCl, 10 mM $CaCl_2$, pH 7.4. The eluted protein was greater than 95% pure after elution as judged by SDS-polyacrylamide gel electrophoresis.

Further purification of the protein was accomplished by making the protein 3 M in NaCl followed by adsorption to a hydrophobic interaction resin (Toyopearl Phenyl 650 M, TosoHaas) equilibrated in 20 mM Tris, 3 M NaCl, 10 mM $CaCl_2$, pH 7.4. After washing with 2 column volumes of equilibration buffer without $CaCl_2$, the recombinant human protein C was eluted with 20 mM Tris, pH 7.4.

The eluted protein was prepared for activation by removal of residual calcium. The recombinant human protein C was passed over a metal affinity column (Chelex-100, Bio-Rad) to remove calcium and again bound to an anion exchanger (Fast Flow Q, Pharmacia). Both of these columns were arranged in series and equilibrated in 20 mM Tris, 150 mM NaCl, 5 mM EDTA, pH 7.4. Following loading of the protein, the Chelex-100 column was washed with one column volume of the same buffer before disconnecting it from the series. The anion exchange column was washed with 3 column volumes of equilibration buffer before eluting the protein with 0.4 M NaCl, 20 mM Tris-acetate, pH 6.5. Protein concentrations of recombinant human protein C and recombinant activated protein C solutions were measured by UV 280 nm extinction $E^{0.1\%}$=1.81 or 1.85, respectively.

PREPARATION 2

Activation of Recombinant Human Protein C

Bovine thrombin was coupled to Activated CH-Sepharose 4B (Pharmacia) in the presence of 50 mM HEPES, pH 7.5 at 4° C. The coupling reaction was done on resin already packed into a column using approximately 5000 units thrombin/mL resin. The thrombin solution was circulated through the column for approximately 3 hours before adding 2-amino-ethanol (MEA) to a concentration of 0.6 mL/L of circulating solution. The MEA-containing solution was circulated for an additional 10–12 hours to assure complete blockage of the unreacted amines on the resin. Following blocking, the thrombin-coupled resin was washed with 10 column volumes of 1 M NaCl, 20 mM Tris, pH 6.5 to remove all non-specifically bound protein, and was used in activation reactions after equilibrating in activation buffer.

Purified r-hPC was made 5 mM in EDTA (to chelate any residual calcium) and diluted to a concentration of 2 mg/mL with 20 mM Tris, pH 7.4 or 20 mM Tris-acetate, pH 6.5. This material was passed through a thrombin column equilibrated at 37° C. with 50 mM NaCl and either 20 mM Tris pH 7.4 or 20 mM Tris-acetate pH 6.5. The flow rate was adjusted to allow for approximately 20 min. of contact time between the r-hPC and thrombin resin. The effluent was collected and immediately assayed for amidolytic activity. If the material did not have a specific activity (amidolytic) comparable to an established standard of aPC, it was recycled over the thrombin column to activate the r-hPC to completion. This was followed by 1:1 dilution of the material with 20 mM buffer as above, with a pH of either 7.4 or 6.5 to keep the aPC at lower concentrations while it awaited the next processing step.

Removal of leached thrombin from the aPC material was accomplished by binding the aPC to an anion exchange resin (Fast Flow Q, Pharmacia) equilibrated in activation buffer (either 20 mM Tris, pH 7.4 or 20 mM Tris-acetate, pH 6.5) with 150 mM NaCl. Thrombin does not interact with the anion exchange resin under these conditions, but passes through the column into the sample application effluent. Once the aPC is loaded onto the column, a 2–6 column volume wash with 20 mM equilibration buffer is done before eluting the bound aPC with a step elution using 0.4 M NaCl in either 5 mM Tris-acetate, pH 6.5 or 20 mM Tris, pH 7.4. Higher volume washes of the column facilitated more complete removal of the dodecapeptide. The material eluted from this column was stored either in a frozen solution (−20° C.) or as a lyophilized powder.

The anticoagulant activity of activated protein C was determined by measuring the prolongation of the clotting time in the activated partial thromboplastin time (APTT) clotting assay. A standard curve was prepared in dilution buffer (1 mg/mL radioimmunoassay grade bovine serum albumin [BSA], 20 mM Tris, pH 7.4, 150 mM NaCl, 0.02% $NaN_3$) ranging in protein C concentration from 125–1000 ng/mL, while samples were prepared at several dilutions in this concentration range. To each sample cuvette, 50 $\mu$L of cold horse plasma and 50 $\mu$L of reconstituted activated partial thromboplastin time reagent (APTT Reagent, Sigma) were added and incubated at 37° C. for 5 min. After incubation, 50 $\mu$L of the appropriate samples or standards were added to each cuvette. Dilution buffer was used in place of sample or standard to determine basal clotting time. The timer of the fibrometer (CoA Screener Hemostasis Analyzer, American Labor) was started immediately after the addition of 50 $\mu$L 37° C. 30 mM $CaCl_2$ to each sample or standard. Activated protein C concentration in samples are calculated from the linear regression equation of the standard curve. Clotting times reported here are the average of a minimum of three replicates, including standard curve samples.

The above descriptions enable one with appropriate skill in the art to prepare aPC for utilization in combination therapy with BPI protein for the treatment of sepsis.

PREPARATION 3

Expression of BPI protein

In order to produce BPI protein and /or BPI protein variants in mammalian cells, the cDNA sequences is inserted into a suitable plasmid vector as described in U.S. Pat. No. 5,171,739, herein incorporated by reference. A suitable vector for such an application is pSV-1, which contains the origin of replication and early and late promoters of SV40, followed by multiple insert coning sites, followed by termination sequences from the hepatitis B surface antigen gene. Also contained in the plasmid are an origin of bacterial DNA replication, and the genes encoding ampicillin resistance and dihydrofolate reductase. Similar vectors have been used to express other foreign genes

[McGrogan, et al. Biotechnology, 6: 172–177]. Vector DNA is prepared for acceptance of BPI protein cDNA sequences by digestion with HindIII and Bam HI, and dephosphorylation with alkaline phosphatase.

A BPI protein cDNA containing insert is prepared for insertion into pSV-1 by inserting encoding full-length BPI protein prepared by digestion of the parent plasmid with appropriate restriction enzymes, for example EcoRI and Bgl II, yielding two DNA fragments containing portions of the BPI protein coding sequence. These two fragments are ligated together into prepared SV-1, and the recombinant clones obtained are screened by restriction enzyme digestion for the presence of the two inserts in the proper orientation.

The construct is verified by restriction digest analysis, and then prepared in amounts sufficient for transfection into CHO cell line DUXB11 cells. Transfection is performed using lipofectin, and the resulting transformed cells are selected in the presence of increasing amounts of methotrexate using standard protocols.

Supernatants from either transfected pools or clones derived from pools are assayed for the presence of endotoxin binding activity by inhibition of TNr release. BPI protein is purified from the selected supernatant by standard procedures known in the art.

PREPARATION 4

Formulation of Activated Protein C

A stable lyophilized formulation of activated protein C was prepared by a process which comprises lyophilizing a solution comprising about 2.5 mg/mL activated protein C, about 15 mg/mL sucrose, about 20 mg/mL NaCl, and a sodium citrate buffer having a pH greater than 5.5 but less than 6.5. Additionally, the stable lyophilized formulation of activated protein C comprises lyophilizing a solution comprising about 5 mg/mL activated protein C, about 30 mg/mL sucrose, about 38 mg/mL NaCl, and a citrate buffer having a pH greater than 5.5 but less than 6.5.

The ratio of aPC:salt:bulking agent (w:w:w) is an important factor in a formulation suitable for the freeze drying process. The ratio varies depending on the concentration of aPC, salt selection and concentration and bulking agent selection and concentration. Particularly, a ratio of about 1 part activated protein C to about 7.6 parts salt to about 6 parts bulking agent is preferred.

A unit dosage formulation of activated protein C suitable for administration by continuous infusion was prepared by mixing activated protein C, NaCl, sucrose, and sodium citrate buffer. After mixing, 4 mL of the solution was transferred to a unit dosage receptacle and lyophilized. The unit dosage receptacle containing about 5 mg to about 20 mg of activated protein C, suitable for administering a dosage of about 0.01 mg/kg/hr to about 0.05 mg/kg/hr to patients in need thereof, was sealed and stored until use.

PREPARATION 5

Pharmaceutical Composition of BPI Protein

A pharmaceutical composition of BPI protein is prepared by a process which comprises the BPI protein at a concentration of 1 mg/ml in citrate buffered saline (5 or 20 mM citrate, 150 mM NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas, Inc., Wilmington, Del.). Another pharmaceutical composition containing BPI protein comprises the BPI protein at a concentration of 2 mg/ml, in 5 mM citrate, 150 mM NaCl, 0.2% poloxamer 188 and 0.002% polysorbate 80. Such combinations are described in U.S. Pat. No. 5,756,464.

EXAMPLE 1

Administering Activated Protein C in Combination with BPI protein in a Double-blinded Placebo-controlled Trial in Human Patients With Sepsis This protocol is a double-blinded placebo-controlled trial in patients with severe sepsis. Patients are treated with placebo, aPC alone, BPI protein alone, or a combination therapy of aPC and BPI protein. BPI protein is administered by continuous infusion at about 100 μg/kg/hr to about 200 μg/kg/hr for about 48 hours. aPC is administered simultaneously by a continuous infusion of about 1 μg/kg/hr to about 50 μg/kg/hr for about 96 hours.

Entry criteria includes three of the four commonly accepted criteria for sepsis (heart rate, respiratory effort, increased/decreased temperature, increase/decrease white blood cell count). The patients also demonstrate some degree of organ dysfunction defined as either shock, decreased urine output, or hypoxemia.

The primary endpoints of this study are: safety as a function of dose and dose duration; and, comparing treatment with aPC alone or BPI protein alone to the ability of aPC in combination with BPI protein to correct coagulopathy as a function of dose and dose duration. A 28-day all cause mortality is the end-point in patients receiving placebo vs. patients receiving aPC in combination with BPI or either agent alone.

Combination therapy with aPC and BPI protein results in a synergy that is safer and more efficacious and reduces the dosages of both aPC and BPI protein necessary to treat sepsis.

We claim:

1. A method of treating a patient suffering from sepsis which comprises, administering 15 μg/kg/hr to about 30 μg/kg/hr of human activated Protein C in combination with 4 μg/kg/hr to about 420 μg/kg/hr of bactericidal/permeability-increasing (BPI) protein.

2. The method according to claim 1, wherein the amount of the activated Protein C is about 20 μg/kg/hr to about 30 μg/kg/hr.

3. The method of claim 1, wherein the amount of the activated Protein C is 24 μg/kg/hr.

4. The method of claim 2, wherein the activated Protein C is administered by continuous infusion for about 1 to about 240 hours.

5. The method of claim 3, wherein the activated Protein C is administered by continuous infusion for about 1 to about 240 hours.

6. The method of claim 2, wherein the BPI protein is administered by continuous infusion for about 1 to about 240 hours.

7. The method of claim 1, wherein the BPI is administered at about 100 μg/kg/hr to about 200 μg/kg/hr.

8. The method of claim 2, wherein the BPI is administered at about 100 μg/kg/hr to about 200 μg/kg/hr.

9. The method of claim 3, wherein the BPI is administered at about 100 μg/kg/hr to about 200 μg/kg/hr.

10. The method of claim 4 wherein the BPI is administered at about 100 μg/kg/hr to about 200 μg/kg/hr.

11. The method of claim 5 wherein the BPI is administered at about 100 μg/kg/hr to about 200 μg/kg/hr.

12. The method of claim 6 wherein the BPI is administered at about 100 µg/kg/hr to about 200 µg/kg/hr.

13. The method of claim 2, wherein as much as one-third of the daily dose of the activated Protein C is administered as a bolus.

14. The method of claim 2 wherein a bolus of the BPI is administered as an intravenous bolus of 0.1 mg/kg to about 10 mg/kg.

15. The method of claim 3 wherein a bolus of the BPI is administered as an intravenous bolus of 0.1 mg/kg to about 10 mg/kg.

16. The method of claim 4 wherein a bolus of the BPI is administered as an intravenous bolus of 0.1 mg/kg to about 10 mg/kg.

17. The method of claim 5 wherein a bolus of the BPI is administered as an intravenous bolus of 0.1 mg/kg to about 10 mg/kg.

18. The method of claim 6 wherein a bolus of the BPI is administered as an intravenous bolus of 0.1 mg/kg to about 10 mg/kg.

19. The method of claim 7 wherein a bolus of the BPI is administered as an intravenous bolus of 0.1 mg/kg to about 10 mg/kg.

20. The method of claim 8 wherein a bolus of the BPI is administered as an intravenous bolus of 0.1 mg/kg to about 10 mg/kg.

\* \* \* \* \*